United States Patent [19]

Kamen et al.

[11] Patent Number: 5,193,990
[45] Date of Patent: Mar. 16, 1993

[54] FLUID MANAGEMENT SYSTEM WITH AUXILIARY DISPENSING CHAMBER

[75] Inventors: Dean L. Kamen, Bedford; Richard J. Lanigan, Concord, both of N.H.

[73] Assignee: Deka Products Limited Partnership, Manchester, N.H.

[21] Appl. No.: 674,818

[22] Filed: Mar. 22, 1991

Related U.S. Application Data

[63] Continuation-in-part of Ser. No. 615,612, Nov. 17, 1990, abandoned, which is a continuation-in-part of Ser. No. 614,806, Nov. 17, 1990, abandoned, which is a continuation-in-part of Ser. No. 523,801, May 15, 1990, Pat. No. 5,088,515, and a continuation-in-part of Ser. No. 345,387, May 1, 1989, Pat. No. 4,976,162, which is a continuation-in-part of Ser. No. 92,481, Sep. 3, 1987, Pat. No. 4,826,482, which is a continuation-in-part of Ser. No. 22,167, Mar. 5, 1987, Pat. No. 4,808,161, and a continuation-in-part of Ser. No. 836,023, Mar. 4, 1986, Pat. No. 4,778,451.

[51] Int. Cl.$^5$ .................. F04B 43/08; F04B 43/12
[52] U.S. Cl. ........................... 417/474; 417/479
[58] Field of Search ..................... 417/474, 479

[56] References Cited

U.S. PATENT DOCUMENTS 4,303,376 12/1981 Siekmann .................. 417/479
4,657,490 4/1987 Abbott ...................... 417/479

Primary Examiner—Richard A. Bertsch
Assistant Examiner—Alfred Basichas
Attorney, Agent, or Firm—Bromberg & Sunstein

[57] ABSTRACT

A system that permits highly accurate flow control, even at very low flow rates, by providing a measurement chamber and an auxiliary dispensing chamber having a volume that is variable between fixed maximum and minimum limits. The maximum volume of the dispensing chamber is substantially smaller than the maximum volume of the measurement chamber used in this type of system. The dispensing chamber can then be filled to its maximum volume from the measurement chamber and thereafter caused to be reduced over time to its minimum volume. Because the maximum and minimum volumes of the dispensing chamber are known, the volume change of the dispensing chamber per unit time is determinable and is the flow rate out of the system.

13 Claims, 2 Drawing Sheets

FLUID MANAGEMENT SYSTEM WITH AUXILIARY DISPENSING CHAMBER

This application is a continuation-in-part of applications Ser. No. 615,612 filed Nov. 17, 1990, now abandoned (for Acoustic Volume Measurement with Fluid Management Capability; hereinafter the "Acoustic Application"), and Ser. No. 614,806 filed Nov. 17, 1990 now abandoned (for an Integral Intravenous Fluid Delivery Device; hereinafter the "Spike Application"), which are continuations-in-part of applications Ser. No. 523,801 filed May 15, 1990, issued Feb. 18, 1990 as U.S. Pat. No. 5,088,515 (for a Valve System with Removable Fluid Interface; hereinafter the "Valve Application") and Ser. No. 345,387 filed May 1, 1989, issued Dec. 11, 1990 as U.S. Pat. No. 4,976,162 (for an Enhanced Pressure Measurement Flow Control System; hereinafter the "System Application"), which is a continuation-in-part of application Ser. No. 092,481 filed Sep. 3, 1987, issued as U.S. Pat. No. 4,826,482, which is a continuation-in-part of application Ser. No. 022,167 filed Mar. 5, 1987, issued as U.S. Pat. No. 4,808,161, and Ser. No. 836,023 filed Mar. 4, 1986, issued as U.S. Pat. No. 4,778,451. These related applications are hereby incorporated herein by reference.

TECHNICAL FIELD

The present invention relates generally to systems for controlling fluid flow, and in particular to medical infusion technology, although other embodiments are possible.

BACKGROUND ART

The discussion of background art in the System Application is hereby incorporated herein by reference.

SUMMARY OF INVENTION

The present invention permits systems of one type described in the System Application and in the Acoustic Application to achieve highly accurate flow control, even at very low flow rates, by providing in a preferred embodiment an auxiliary dispensing chamber having a volume that is variable between fixed maximum and minimum limits. In a preferred embodiment the maximum volume of the dispensing chamber is substantially smaller than the maximum volume of the measurement chamber used in this type of system. The dispensing chamber can then be filled to its maximum volume from the measurement chamber and thereafter caused to be reduced over time to its minimum volume. Because the maximum and minimum volumes of the dispensing chamber are known, the volume change of the dispensing chamber per unit time is determinable and is the flow rate out of the system.

BRIEF DESCRIPTION OF THE DRAWINGS

The foregoing features of the invention will be more readily understood by reference to the following description taken with the accompanying drawings, in which.

DETAILED DESCRIPTION OF SPECIFIC EMBODIMENTS

Figure 1:
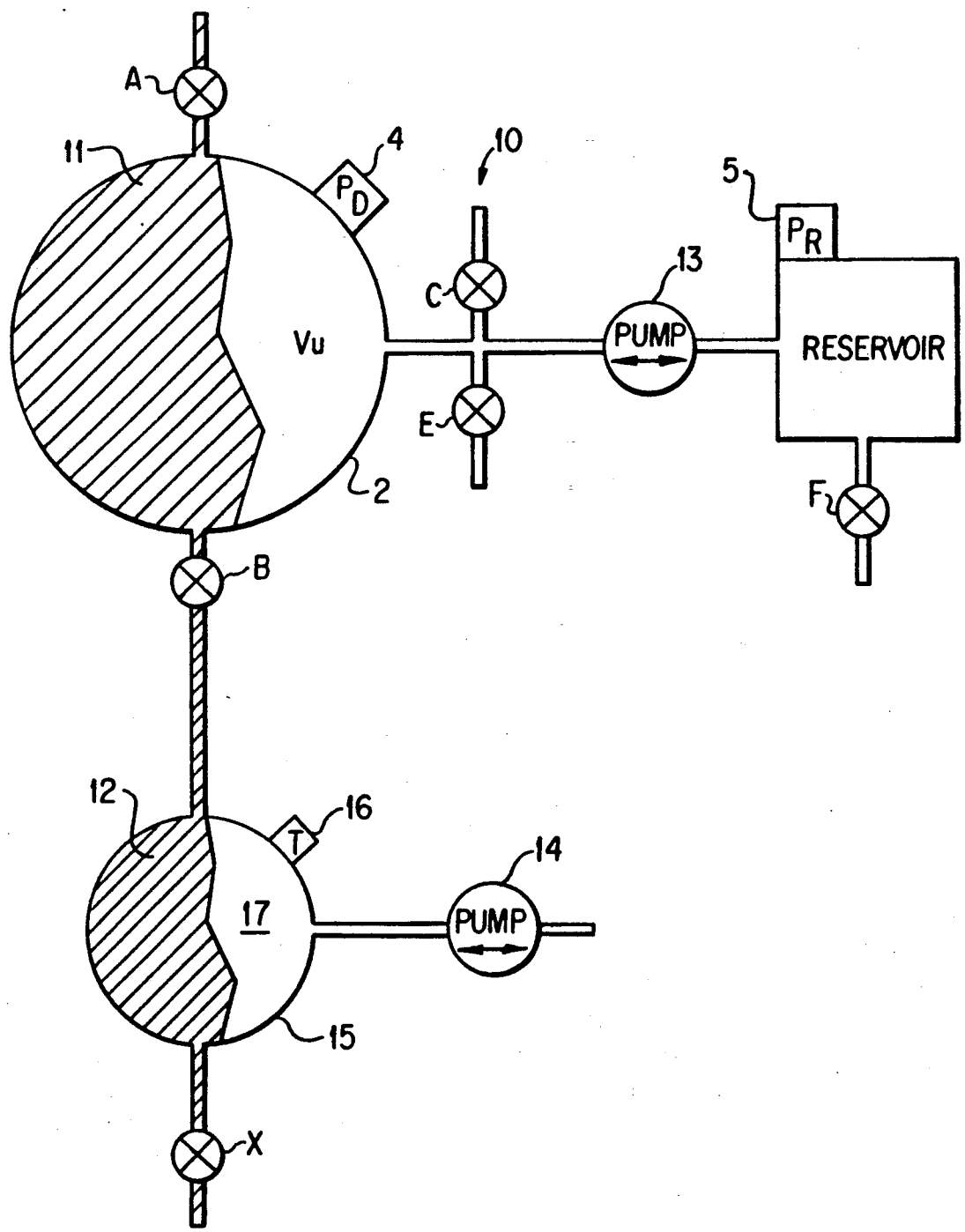
FIG. 1 shows an embodiment of the invention applicable to a control system of the type using Boyle's Law described in the System Application.

The System Application describes a highly accurate system for controlling fluid flow, using a container having a first region into and out of which fluid flows and a second region in which the pressure changes of a measurement gas are monitored, in relation to those in a fixed reference volume, as the basis for flow measurement. Boyle's Law is used to determine the volume of the second region, and because the combined volume of the first and second regions is constant (i.e., equal to the interior volume of the container), the volume of the first region is known. The first region of the container may be embodied in a housing unit having an indentation covered by a membrane to form a measurement chamber into and out of which fluid flows; the housing unit may also include suitable fluid passageways and valves. The housing unit can be affixed to a receiving block in such a way that the measurement chamber abuts a sealed indentation in the block defining the second region of the container. The Acoustic Application describes an improvement in which static pressure need not be measured and the volume of the second region is determined acoustically as the basis for flow measurement.

The present invention permits systems of the foregoing type to achieve highly accurate flow control, even at very low flow rates, by providing in a preferred embodiment an auxiliary dispensing chamber having a volume that is variable between fixed maximum and minimum limits. In a preferred embodiment the maximum volume of the dispensing chamber is substantially smaller than the maximum volume of the first region. The dispensing chamber can then be filled to its maximum volume from the measurement chamber and thereafter caused to be reduced over time to its minimum volume. Because the maximum and minimum volumes of the dispensing chamber are known, the volume change of the dispensing chamber per unit time is determinable and is the flow rate out of the system. (Of course, the system can be used to pump in the other direction, in which case the flow direction would be into the system.)

In a preferred embodiment, the dispensing chamber may be embodied in a manner analogous to the measurement chambers described as item 71 in FIGS. 7-10 of the System Application. It may thus be formed in a housing having an indentation covered by a membrane. The pressure of a suitable measurement gas such as air is used to move the membrane and change the volume of the dispensing chamber. Valving associated with the dispensing chamber may be constructed in a manner similar to valving associated with the measurement chamber. Pressure in the dispensing chamber may be monitored in the manner of pressure in the measurement chamber, namely by monitoring measurement gas pressure in the region on the other side of the membrane.

As an example, assume that the dispensing chamber's volume change between maximum and minimum limits is one-tenth the maximum volume change of the first region, i.e. of the measurement chamber. The dispensing chamber may thus undergo ten fill-and-empty cycles before the measurement chamber needs to be refilled. Also preferably, the volume of the measurement gas region associated with the dispensing chamber is correspondingly smaller than the volume of the measurement gas region associated with the measurement chamber. This means that there can be a significant pressure change in the dispensing chamber as it fills or empties, and this pressure change can be used, if desired, to determine the volume of fluid remaining in the dispensing chamber. Alternatively, acoustic volume measurement technology may be used in the manner described in the Acoustic Application, or any other suitable means of volume measurement may be employed. In this manner, flow from the dispensing chamber over a fill-and-empty cycle in a given period of time may be monitored with approximately the same precision as flow from the measurement chamber over a fill-and-empty cycle in the same period of time, even though (in this example) the flow from the dispensing chamber is at approximately one tenth the rate of flow from the measurement chamber. Effectively, the present invention increases the dynamic range over which flow control is possible. Moreover, although short-term flow control may be achieved by tracking and controlling the fill-and-empty cycles of the dispensing chamber, long-term flow control may be achieved by reference to the fill-and-empty cycles of the measurement chamber. In particular total delivered volume data derived from the measurement chamber may be used to update rate control data derived from the dispensing chamber. One method in which short-term flow rate control may be updated by total delivered volume data is disclosed in U.S. Pat. No. 4,634,426, for an invention of Dean Kamen entitled "Medical Infusion Controller and User Interface", which is hereby incorporated herein by reference.

In a related preferred embodiment, there is no intermediate determination of the volume of fluid in the dispensing chamber, and the chamber is simply moved between its maximum and minimum volume limits. With each "binary" fill-and-empty cycle of the dispensing chamber, a known amount of fluid has been dispensed, and this fact permits control of the fluid flow. In such an embodiment, no pressure transducer associated with the dispensing chamber is required, nor is any other means of intermediate tracking of the volume of fluid in the dispensing chamber. The measurement chamber may be used to assure long-term flow control in the manner described in the previous paragraph.

In FIG. 1 is shown an embodiment of the invention applicable to a control system 10 of the type using Boyle's Law described in connection with FIG. 5 of the System Application. The container 2 has a measurement region 11 of variable volume occupied by fluid and a second region Vu occupied by a measurement gas such as air. Valves A and B are disposed in the fluid path into and out of the container. A pressure transducer 4 determines the pressure $P_D$ of measurement gas in the container. Preferably, the measurement gas and the fluid are separated in the container by a suitable pressure-communicating arrangement such as a flexible membrane (forming the measurement region 11 into a measurement chamber) so that the pressure transducer 4 also determines the pressure of the fluid in the measurement chamber 11. A pump 13 pumps measurement gas between the second region Vu and a reservoir of known volume, the pressure of which is monitored by transducer 5. Boyle's law is used to determine the volume of Vu and hence the volume occupied by fluid in measurement chamber 11.

In the fluid path below valve B is the dispensing region 12 of a second container 15 also having a second region 17 occupied by measurement gas. Preferably, as in the case of the first container, the measurement gas and the fluid are separated in the container by a suitable pressure-communicating arrangement such as a flexible membrane (forming the dispensing region 12 into dispensing chamber 12). A pump 14 pumps gas in and out of the second region 17 to vary the volume of the dispensing region between fixed maximum and minimum limits. The pressure in the container may, in accordance with some embodiments, be monitored by optional transducer 16. The valve X in the fluid path below dispensing region 12 works in cooperation with valve B to permit the isolation of the fluid in the dispensing region from pressure effects elsewhere in the line. This isolation is achieved in a manner equivalent to the isolation of the measurement region 11 by valves A and B as described in the System Application.

Figure 2:
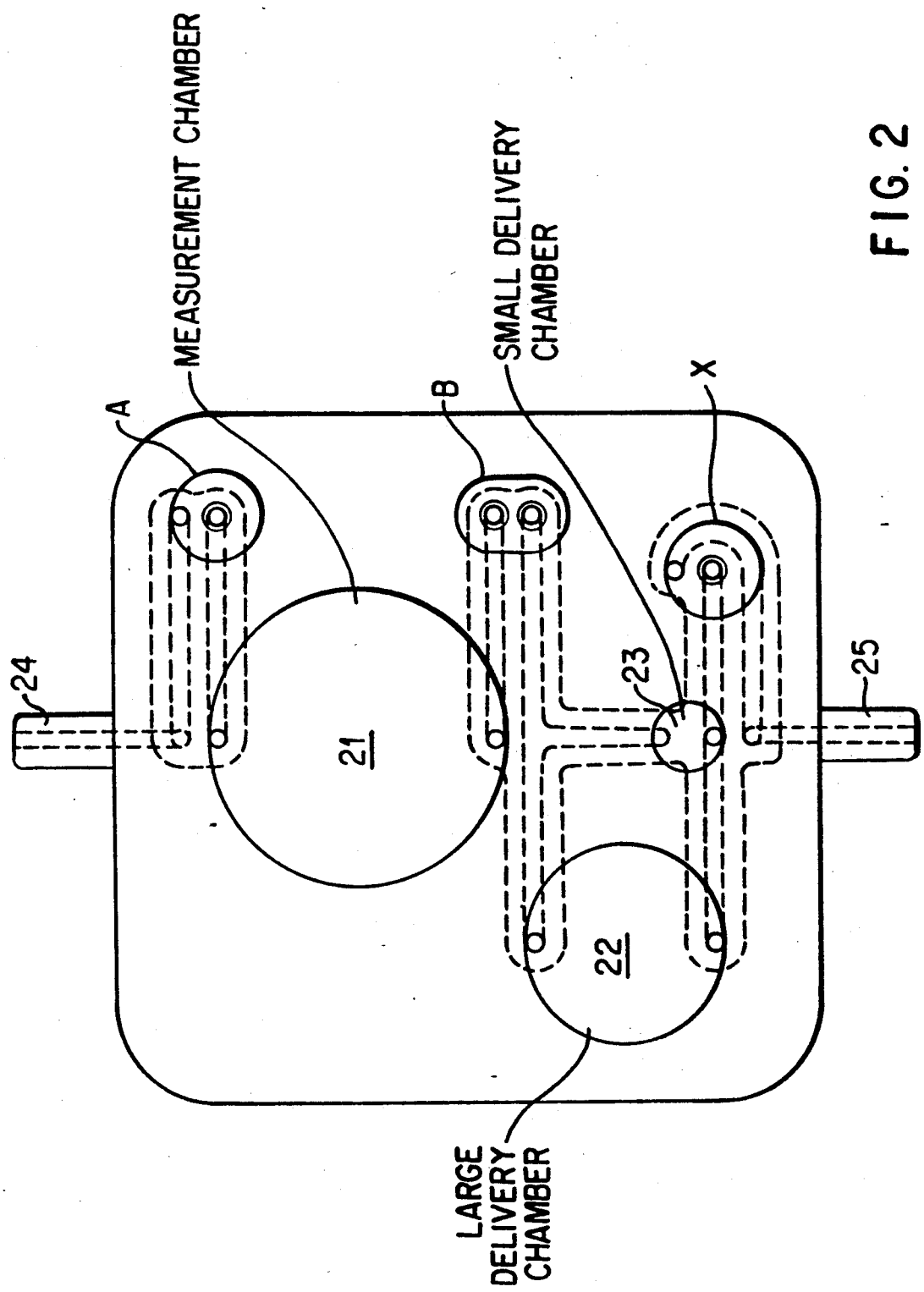
FIG. 2 shows an embodiment of the invention utilizing two auxiliary dispensing chambers in a disposable format similar to that described in the System Application.

FIG. 2 shows an embodiment of the invention utilizing two auxiliary dispensing chambers in a disposable format similar to that described in relation to FIGS. 7-9 and 11-12 of the System Application. The relations of measurement chamber 21, first dispensing chamber 22, and valves A, B, and X are the same as shown in FIG. 1. In this case, however, in the fluid path, in parallel with that of the first dispensing chamber 22, and disposed between valves B and X, is a second (smaller) dispensing chamber 23. In this embodiment, valve B is of the same type as shown in FIG. 6B of the System Application and valves A and X are of the type shown in FIG. 6A of the System Application. The fluid path is from the inlet 24 through the dashed passageways shown to valve A, then measurement chamber 21, valve B, then to both dispensing chambers 22 and 23, then to valve X, then to outlet 25. It is intended that each of the foregoing chambers is formed by an indentation in a housing unit covered by a membrane and each chamber abuts a corresponding indentation in a receiving block defining a region into and out of which gas may be pumped to affect the pressure of fluid in the chamber, and, depending on the position of valves A, B, and X, to pump fluid.

Operation of the two dispensing chambers is as follows. Gas pressure may be used to place either or both of the dispensing chambers 22 and 23 at minimum volume. If both are maintained at minimum volume, valve X can remain open, and the system behaves like the system shown in FIG. 5 of the System Application. Alternatively, one of the dispensing chambers may maintained at minimum volume, and the other dispensing chamber may be used in the manner described above in connection with FIG. 1. In this manner, the fluid flow control range may be selected depending on whether the larger dispensing chamber 22 or the smaller dispensing chamber 23 is used actively. As a further embodiment, both of the dispensing chambers may be simultaneously filled and emptied, creating an effective dispensing chamber volume larger than either dispensing chamber alone.

The use of the dispensing chambers in these embodiments is intended to be illustrative but not exhaustive of the possible applications of the present invention. One or more dispensing chambers for example may be used as part of the integral intravenous fluid delivery device shown in FIG. 6 of the Spike Application and may be used in the embodiments of FIG. 7 of the System Application and in embodiments shown in the Valve Application.

What is claimed is:

1. A system for controlling the flow of fluid through a line, comprising:
   (a) first, second, and third valves in series in the line;
   (b) a container having first and second regions of variable volume, the first region disposed in fluid communication between the first and second valves;
   (d) dispensing chamber means for providing a first dispensing volume, variable between first fixed maximum and minimum limits, disposed in fluid communication between the second and third valves;
   (e) volume determination means for determining the volume of fluid in the first region by means of a measurement gas in the second region;
   (f) control means, in communication with the volume determination means, the first, second and third valves, the pressure means, and the dispensing chamber means for directing the operation of the valves, the pressure means, and the dispensing means to produce the desired flow through the line.

2. A system according to claim 1, further comprising: second dispensing chamber means for providing a second dispensing volume, variable between second fixed maximum and minimum limits, disposed in fluid communication between the second and third valves, and in communication with the control means.

3. A system according to claim 1, wherein the dispensing chamber means includes an associated region of variable volume having a common boundary with the dispensing volume in such a way that the combined volume of the dispensing volume and the associated region is constant, and further comprising:
   dispensing pressure means, for varying the pressure of a gas in the associated region, in communication with the control means.

4. A system according to claim 3, further comprising:
   a housing;
   a flexible membrane disposed on the housing, the membrane having an internal side facing the housing and an external side facing away from the housing,
   the housing and the membrane defining (i) the first region, (ii) the first dispensing volume, and (iii) valving chamber means associated with each of the first, second, and third valves, for providing valving in response to pressure on the external side of the membrane in the vicinity of the valving chamber means.

5. An assembly for controlling the flow of fluid through a line, comprising:
   a housing;
   a flexible membrane disposed on the housing, the membrane having an internal side facing the housing and an external side facing away from the housing,
   the housing and the membrane defining
   (i) first, second and third valving chambers for providing valving in response to pressure on the external side of the membrane in the vicinity of the valving chamber, the valves disposed in series in the line, each of the valves further having first and second mouths for providing fluid communication with the line; (ii) a first region of variable volume disposed in fluid communication between the first and second valving chambers, and (iii) a dispensing volume, variable between fixed maximum and minimum limits, disposed in fluid communication between the second and third valving chambers.

6. A system according to claim 5, wherein the housing and the membrane further define a second dispensing volume, variable between second fixed maximum and minimum limits, disposed in fluid communication between the second and third valving chambers.

7. A system according to claim 5, wherein the first dispensing volume at its maximum limit is smaller than the first region's volume at its maximum.

8. A system according to claim 6, wherein the first dispensing volume at its maximum limit is smaller than the first region's volume at its maximum, and the second dispensing volume at its maximum limit is smaller than the first dispensing volume at its maximum limit.

9. A system according to claim 1, wherein the dispensing chamber is located downstream of the container.

10. A system according to claim 1, wherein the first dispensing volume at its maximum limit is smaller than the container's volume at its maximum.

11. A system according to claim 2, wherein the first dispensing volume at its maximum limit is smaller than the container's volume at its maximum, and the second dispensing volume at its maximum limit is smaller than the first dispensing vole at its maximum limit.

12. A system according to claim 2, wherein the two dispensing chambers are located downstream of the container.

13. A system according to claim 12, wherein the first dispensing volume at its maximum limit is smaller than the container's volume at its maximum, and the second dispensing volume at its maximum limit is smaller than the first dispensing volume at its maximum limit.

* * * * *